United States Patent [19]

Higuchi et al.

[11] Patent Number: 4,754,086

[45] Date of Patent: Jun. 28, 1988

[54] PROCESS FOR PREPARATION OF NUCLEAR HALIDES OF MONOALKYLBENZENES

[75] Inventors: Yasushi Higuchi; Toshihiro Suzuki, both of Shizuoka, Japan

[73] Assignee: Ihara Chemical Industry Co., Ltd., Tokyo, Japan

[21] Appl. No.: 882,196

[22] Filed: Jul. 3, 1986

Related U.S. Application Data

[63] Continuation of Ser. No. 715,777, Mar. 26, 1985, abandoned, which is a continuation of Ser. No. 564,527, Dec. 22, 1983, abandoned.

[30] Foreign Application Priority Data

Dec. 22, 1982 [JP] Japan .................................. 57-225259
May 13, 1983 [JP] Japan .................................. 58-83677

[51] Int. Cl.[4] ............................................. C07C 17/12
[52] U.S. Cl. ..................................... 570/208; 570/147; 570/206
[58] Field of Search ...................... 570/206, 208, 147

[56] References Cited

U.S. PATENT DOCUMENTS

| 2,998,459 | 8/1961 | Baker et al. | 570/207 |
| 3,216,789 | 11/1965 | Breck et al. | 23/113 |
| 3,706,694 | 12/1972 | Young | 502/74 |
| 3,752,856 | 8/1973 | Nacy et al. | 570/206 |
| 3,945,943 | 3/1976 | Ward | 502/64 |

FOREIGN PATENT DOCUMENTS

| 2721640 | 11/1978 | Fed. Rep. of Germany | 570/208 |
| 55-153400 | 10/1980 | Japan . | |
| 31627 | 2/1982 | Japan | 570/208 |
| 77631 | 5/1982 | Japan | 570/206 |
| 650985 | 3/1979 | U.S.S.R. | 570/208 |

OTHER PUBLICATIONS

Huizinga et al., "Tetrahedron Letters," vol. 21, (1980), pp. 3809–3812.

Primary Examiner—J. E. Evans
Attorney, Agent, or Firm—Oblon, Fisher, Spivak, McClelland & Maier

[57]   ABSTRACT

A nuclear halide of a monoalkylbenzene is prepared by halogenating a monoalkylbenzene in the presence of an L-type zeolite catalyst.

12 Claims, No Drawings

PROCESS FOR PREPARATION OF NUCLEAR HALIDES OF MONOALKYLBENZENES

This application is a continuation of application Ser. No. 715,777 filed Mar. 26, 1985 now abandoned, which in turn is a continuation of application Ser. No. 564,527, filed Dec. 22, 1983, now abandoned.

BACKGROUND OF THE INVENTION (1) Field of the Invention

This invention relates to a process for the preparation of a nuclear halide of a monoalkylbenzene. More particularly, the present invention relates to a process for preparing a p-halogeno-monoalkylbenzene at a high selectivity by nuclear halogenation of a monoalkylbenzene in the presence of a specific catalyst.

(2) Description of the Prior Art

Nuclear halides of monoalkylbenzenes are valuable as starting materials for the synthesis of medicines, agricultural chemicals, and other various organic compounds of these, p-chloro-monoalkylbenzenes, for example, p-chlorotoluene, are in especially great demand.

As a conventional process for the preparation of nuclear halides of monoalkylbenzenes, there is known a process in which a monoalkylbenzene is subjected to nuclear halogenation by using a Lewis acid such as antimony chloride, ferric chloride, or aluminum chloride as a catalyst and a chlorine gas as a chlorinating agent. In this process, an o-chloro-monoalkylbenzene is formed as a main product and an m-chloro-monoalkylbenzene and polychlorinated substitution products are formed as by-products. It is impossible, however, to prepare the p-chloro-monoalkylbenzene in a yield higher than 40%.

Various catalysts have therefore been developed so as to produce p-chloro-monoalkylbenzenes in high yields. For example, in a process using a Lewis acid and sulfur or selenium as the catalyst, a p-chloro-monoalkylbenzene is obtained in a yield of 45% to 52%. In a process using a Lewis acid and thianthrene as the catalyst, a p-chloro-monoalkylbenzene is obtained in a yield of 55% to 60% (see U.S. Pat. No. 4,031,147 and British Pat. No. 7,605,039). Furthermore, in a process using a Lewis acid and phenoxthine as the catalyst, a p-chloro-monoalkylbenzene is obtained in a yield of 52% to 60% (see European Pat. No. 63384).

As another process for preparing a nuclear halide of a monoalkylbenzene, there is known a process in which silica gel is used as the catalyst and sulfuryl chloride is used as the halogenating agent. In this process, a p-chloro-monoalkylbenzene is obtained in a yield of 50% [see Journal of Synthetic Organic Chemistry, 37, page 690 (1979) (Japan)].

However, all of these known processes are still insufficient in the selectivity to p-chloro-monoalkylbenzenes.

SUMMARY OF THE INVENTION

It is a primary object of the present invention to provide a process by which a p-halogeno-monoalkylbenzene can be prepared at a higher selectivity than in the conventional processes.

In accordance with the present invention, there is provided a process for preparing a nuclear halide of a monoalkylbenzene by halogenating a monoalkylbenzene in the presence of a catalyst. The process is characterized in that an L-type zeolite is used as the catalyst.

DESCRIPTION OF THE PREFERRED EMBODIMENTS

The L-type zeolite used in the process of the present invention is a crystalline aluminosilicate in which the silicon dioxide ($SiO_2$)/aluminum oxide ($Al_2O_3$) molar ratio is in the range of from 4 to 8. Ordinarily, a synthetic zeolite or natural zeolite having the same X-ray diffraction spectrum as that of this crystalline aluminosilicate can be used in the present invention. An L-type zeolite containing potassium as the ion-exchangeable cation is ordinarily available. In this zeolite, of course, potassium may be ion-exchanged with sodium. A known ion exchange method may appropriately be employed for this ion exchange. Ordinarily, the ion exchange can easily be accomplished by treating the potassium-containing L-type zeolite with an aqueous solution of a nitrate or chloride of sodium. The L-type zeolite used in the present invention may contain a cation other than the potassium ion, and the zeolite ion-exchanged with a metal of the Group IA (other than sodium), IIA, IIIA, IVA, or VA in the periodic table, a transition metal or proton is preferably used. These cations may be included either alone or in combination in the zeolite. The catalyst may be used either in the uncalcined state or in the calcined state.

Various linear and branched monoalkylbenzenes can be halogenated according to the process of the present invention. Monoalkylbenzenes having 1 to 4 carbon atoms in the alkyl group are preferred.

For preparing a nuclear halide of a monoalkylbenzene according to the process of the present invention, an L-type zeolite is added to a monoalkylbenzene in an amount of at least 0.01 g, preferably 0.1 to 50 g, and more preferably 1 to 30 g, per mole of the monoalkylbenzene so that the mixture can be stirred, and a halogenating agent is introduced in the mixture at a temperature lower than the boiling point to effect reaction between the monoalkylbenzene and the halogenating agent. A reaction solvent may be used if desired. The reaction temperature is not particularly critical, but it is preferred that the reaction be carried out at a temperature higher than 0° C. but lower than the boiling point.

Halogenating agents customarily used in this field may be used in the present invention. For example, a halogen such as chlorine gas or bromine and sulfuryl halides such as sulfuryl chloride may be used. Among these, sulfuryl chloride is most preferably used.

An inert gas such as nitrogen may be used for the reaction. The reaction may be carried out under an elevated or reduced pressure, but ordinarily, the reaction is carried out under atmospheric pressure.

According to the process of the present invention, the p-position of a monoalkylbenzene can be effectively halogenated at a high selectivity while controlling halogenation at the o-position of a monoalkylbenzene. Moreover, the process of the present invention is advantageous in that formation of side chain halides of monoalkylbenzenes such as benzyl halides and polynuclear halides can be greatly controlled. Furthermore, the reaction and post treatment operations are very simple and the catalyst can be used repeatedly. Therefore, the process of the present invention is very suitable for the production of p-halogeno-monoalkylbenzenes.

The process of the present invention will now be described in detail with reference to the following examples.

EXAMPLE 1

A 200-ml reaction flask equipped with a cooling tube, a thermometer, a stirrer and a blow tube was charged with 5 g of an L-type zeolite (Trademark "TSZ-502" supplied by TOYO SODA MANUFACTURING CO., LTD., Japan) and 92.1 g (1 mole) of toluene. The mixture was stirred at 70° C. for 30 minutes in a current of $N_2$. Then, chlorine was blown into the flask at a rate of 0.29 mole per hour. The reaction was conducted for 4 hours. After completion of the reaction, the obtained liquid mixture was analyzed by gas chromatography. As a result, it was found that the conversion of toluene was 97.9%, the 2-chlorotoluene/4-chlorotoluene molar ratio (hereinafter referred to "O/P ratio" for brevity) in the formed chrolotoluene product was 0.5, and benzyl chloride was formed in a yield of 0.92%.

The L-type zeolite used for the reaction had the following chemical composition (as determined by atomic absorption spectroscopy):
$SiO_2$: 64.6% by weight (dry base)
$Al_2O_3$: 17.8% by weight (dry base)
$Na_2O$: 0.15% by weight (dry base)
$SiO_2/Al_2O_3$ molar ratio: 6.2
$K_2O$: 15.9% by weight (dry base)

COMPARATIVE EXAMPLE 1

The reaction was carried out in the same manner as described in Example 1, except that an X-type zeolite (Trademark "TSZ-201" supplied by TOYO SODA MANUFACTURING CO., LTD., Japan) was used instead of the L-type zeolite.

It was found that the conversion of toluene was 85.0% and the O/P ratio was 1.74, and benzyl chloride was formed in a yield of 4.3%.

The X-type zeolite used for the reaction had the following chemical composition (as determined by atomic absorption spectroscopy):
$SiO_2$: 47.2% by weight (dry base)
$Al_2O_3$: 31.7% by weight (dry base)
$Na_2O_3$: 18.5% by weight (dry base)
$SiO_2/Al_2O_3$ molar ratio: 2.5

EXAMPLES 2 through 4

The reaction was carried out in the same manner as described in Example 1, except that the reaction temperature and the amount of the L-type zeolite used were changed as indicated in Table 1. The obtained results are shown in Table 1.

TABLE 1

| Example No. | Amount (g) of L-type zeolite | Reaction temperature (°C.) | Conversion (%) | O/P Ratio |
| --- | --- | --- | --- | --- |
| 2 | 1 | 70 | 84.5 | 0.49 |
| 3 | 5 | 90 | 98 | 0.48 |
| 4 | 5 | 110–120 | 95 | 0.56 |

EXAMPLE 5

The reaction was carried out in the same manner as described in Example 1, and then the catalyst was used again for the reaction could be advanced normally, and the O/P ratio was 0.52. The catalyst could be used further.

EXAMPLE 6 THROUGH 9

The reactions were carried out in the same manner as described in Example 1, except that the alkylbenzenes shown in Table 2 were used instead of the toluene used in Example 1, whereby a nuclear chloride of the monoalkylbenzene, shown in Table 2, was obtained. The obtained results are shown in Table 2. Incidentally, the O/P ratio in Table 2 indicates the o-chloro-monoalkylbenzene/p-chloro-monoalkylbenzene molar ratio in the formed nuclear chloride of monoalkylbenzene.

TABLE 2

| Example No. | Monoalkylbenzene to be halogenated | Conversion (%) of alkylbenzene | Nuclear chloride of monoalkylbenzene | O/P ratio |
| --- | --- | --- | --- | --- |
| 6 | Ethylbenzene | 94.9 | Chloroethylbenzene | 0.33 |
| 7 | Isopropylbenzene | 90.7 | Chloroisopropyl benzene | 0.26 |
| 8 | Sec-Butylbenzene | 77.4 | Chloro-sec-butyl benzene | 0.17 |
| 9 | tert-Butylbenzene | 70.5% | Chloro-tert-butyl benzene | 0.06 |

EXAMPLE 10

The reaction was carried out in the same manner as described in Example 1, except that sulfuryl chloride was used as the halogenating agent instead of the chlorine gas used in Example 1 and 35.2 g (1.002 moles) of sulfuryl chloride was dropped over a period of 3.5 hours.

It was found that the conversion of toluene was 99.6%, the O/P ratio was 0.32, and benzyl chloride was formed as a by-product in a yield of 0.8%.

We claim:

1. A process for preparing a nuclear halide of a monoalkylbenzene, the alkyl group of which has 1 to 4 carbon atoms, by halogenating a monoalkylbenzene in a liquid phase in the presence of a catalyst, characterized in that an L-type zeolite is used as the catalyst, whereby a p-halogeno-monoalkylbenzene is prepared at an enhanced selectivity.

2. A process according to claim 1, wherein the amount of the L-type zeolite is at least 0.01 g per mole of the monoalkylbenzene.

3. A process according to claim 1, wherein the amount of the L-type zeolite is in the range of from 0.1 to 50 g per mole of the monoalkylbenzene.

4. A process according to claim 1, wherein chlorine gas or bromine is used as a halogenating agent.

5. A process according to claim 1, wherein a sulfuryl halide is used as a halogenating agent.

6. A process according to claim 5, wherein the sulfuryl halide is sulfuryl chloride.

7. A process according to claim 1 wherein the monoalkylbenzene is halogenated at a temperature higher than 0° C. but lower than the boiling point.

8. A process according to claim 1 wherein the L-type zeolite contains, as an ion-exchangeable cation, potassium and at least one cation selected from the group consisting of protons, metals of groups IA, IIA, IIIA, IVA and VA in the periodic table and transition metals.

9. A process according to claim 1 wherein the L-type zeolite contains potassium as an ion-exchangeable cation.

10. A process according to claim 1 wherein the monoalkylbenzene is toluene.

11. A process according to claim 10, wherein the monoalkylbenzene is chlorinated.

12. A process for preparing p-chlorotoluene by chlorinating toluene in a liquid phase in the presence of a catalyst at a temperature higher than 0° C. but lower than the boiling point of the said liquid phase, characterized in that an L-type zeolite containing potassium as an ion-exchangeable cation is used as the catalyst in an amount of from 0.1 to 50 grams per mole of toluene, whereby p-chlorotoluene is obtained at an enhanced selectivity.

* * * * *